United States Patent
Parsonage (10) Patent No.: US 7,758,635 B2
(45) Date of Patent: Jul. 20, 2010

(54) MEDICAL DEVICE INCLUDING CYLINDRICAL MICELLES

(75) Inventor: Edward Parsonage, St. Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 515 days.

(21) Appl. No.: 11/674,403

(22) Filed: Feb. 13, 2007

(65) Prior Publication Data
US 2008/0195192 A1 Aug. 14, 2008

(51) Int. Cl.
*A61F 2/06* (2006.01)
(52) U.S. Cl. ...................... 623/1.41; 623/2.1
(58) Field of Classification Search .......... 623/1.1–1.54
See application file for complete search history.

(56) References Cited

U.S. PATENT DOCUMENTS

| | | | |
|---|---|---|---|
| 6,338,859 B1 | 1/2002 | Leroux et al. | |
| 6,364,856 B1 | 4/2002 | Ding et al. | |
| 6,730,117 B1 | 5/2004 | Tseng et al. | |
| 6,776,793 B2 | 8/2004 | Brown et al. | |
| 6,780,849 B2 | 8/2004 | Herrmann et al. | |
| 6,861,088 B2 | 3/2005 | Weber et al. | |
| 6,945,993 B2 | 9/2005 | Kveen et al. | |
| 6,979,473 B2 | 12/2005 | O'Connor et al. | |
| 6,981,986 B1 | 1/2006 | Brown et al. | |
| 6,991,802 B1 | 1/2006 | Ahola et al. | |
| 7,105,175 B2 | 9/2006 | Schwarz | |
| 7,179,864 B2 | 2/2007 | Wang | |
| 7,211,108 B2 | 5/2007 | Furst et al. | |
| 7,235,295 B2 | 6/2007 | Laurencin et al. | |
| 2004/0047891 A1 | 3/2004 | Glozman et al. | |
| 2005/0003016 A1 | 1/2005 | Discher et al. | |
| 2005/0131528 A1 | 6/2005 | Buscemi et al. | |
| 2005/0180922 A1 | 8/2005 | Discher et al. | |
| 2005/0192662 A1 | 9/2005 | Ward | |
| 2006/0045901 A1 | 3/2006 | Weber | |
| 2006/0165810 A1 | 7/2006 | Discher et al. | |
| 2006/0240092 A1 | 10/2006 | Breitenkamp et al. | |
| 2007/0125247 A1 | 6/2007 | Kunstmann et al. | |
| 2007/0244569 A1* | 10/2007 | Weber et al. | 623/23.75 |

FOREIGN PATENT DOCUMENTS

| | | |
|---|---|---|
| WO | 2004087251 A1 | 10/2004 |
| WO | 2005046747 A2 | 5/2005 |
| WO | 2007024552 A2 | 3/2007 |
| WO | 2007078516 A2 | 7/2007 |

OTHER PUBLICATIONS

Yoshimoto, H., et al., "A Biodegradable Nanofiber Scaffold by Electrospinning and Its Potential for Bone Tissue Engineering," Biomaterials, 24 (2003) pp. 2077-2082.

Jain, Sumeet et al., "On the Origins of Morphological Complexity in Block Copolymer Surfactants," Science, vol. 300, Apr. 18, 2003, pp. 460-464.

* cited by examiner

*Primary Examiner*—William H. Matthews
*Assistant Examiner*—Jonathan Stroud
(74) *Attorney, Agent, or Firm*—Crompton, Seager & Tufte, LLC (57) ABSTRACT

An endovascular stent comprising an expandable framework including a plurality of interconnected segments, and a plurality of entangled cylindrical micelles disposed on the expandable framework. Each of the plurality of cylindrical micelles may be loaded with a therapeutic agent.

20 Claims, 4 Drawing Sheets

MEDICAL DEVICE INCLUDING CYLINDRICAL MICELLES

TECHNICAL FIELD

The present disclosure generally relates to medical devices including cylindrical micelles placed therewith. More specifically, the disclosure pertains to prostheses, such as prosthetic grafts and endovascular stents incorporating cylindrical micelles.

BACKGROUND

Implantable medical devices, such as prosthetic grafts or endovascular stents, are used frequently in medical procedures. For instance, endovascular stents have been found useful in the treatment and repair of blood vessels after a stenosis has been treated by percutaneous transluminal coronary angioplasty (PTCA), percutaneous transluminal angioplasty (PTA), or other medical procedure in which the patency and/or integrity of a vessel lumen is improved. Stents may also be used to provide patency/integrity of a vessel lumen across a stenosis in cases in which no initial PTCA or PTA procedure is performed. Stents have also garnered beneficial results in other applications. For instance, stents may also be implanted in other body lumens or vessels, such as the urethra, esophagus, bile duct, or the like in order to improve the patency/integrity of the body lumen and/or vessel.

Once a stent is placed in a body lumen, it may be desirable to promote tissue growth on and/or around the stent to insure healing after a medical procedure. Thus, there is an ongoing desire to provide improved stent structures, constituents and/or arrangements which promote tissue growth on and/or around a stent within a body lumen to insure suitable healing after implantation of the stent.

Additionally or alternatively, during some medical procedures it may be advantageous to provide a therapeutic agent, such as a pharmacological substance or drug, at the location in which the stent is positioned during placement of the stent. Stents incorporating a pharmacological substance have been devised for this purpose. Drug-releasing stent devices have shown great potential in treating coronary artery disease, as well as in other treatment situations. As the use of drug-releasing stent devices becomes more frequent, there is an ongoing desire to provide improved techniques involving the incorporation and/or release of a therapeutic agent, such as a pharmacological substance, for delivery with an endovascular stent.

SUMMARY

The disclosure is directed to prostheses, such as prosthetic grafts and endovascular stents incorporating cylindrical micelles.

Accordingly, one illustrative embodiment is a stent comprising an expandable framework including a plurality of interconnected undulating segments, and a plurality of cylindrical micelles incorporated with the expandable framework. Each of the plurality of cylindrical micelles may be loaded with a therapeutic agent.

Another illustrative embodiment is an endovascular stent comprising an expandable framework including a plurality of interconnected segments which can include undulating segments, and a plurality of cylindrical micelles entangled to form a three-dimensional fibrous construct of cylindrical micelles, wherein a discrete cylindrical micelle is discernible from an adjacent cylindrical micelle within the fibrous construct of cylindrical micelles. The fibrous construct of cylindrical micelles is disposed on the expandable framework. A portion of the radially outward facing surface and/or a portion of the radially inward facing surface of the expandable framework may be accessible through the fibrous construct of cylindrical micelles. Each of the plurality of entangled cylindrical micelles may be loaded with a therapeutic agent.

Another illustrative embodiment is a method of forming a drug releasing medical device. Initially, a plurality of cylindrical micelles may be assembled in a solution. Each cylindrical micelle has an outer shell including a first polymer block surrounding a core region including a second polymer block. The first polymer block is more soluble in the solution than the second polymer block. The plurality of cylindrical micelles may be loaded with a therapeutic agent. Additionally, the plurality of cylindrical micelles are stabilized into solidified filaments. The plurality of cylindrical micelles are placed on a medical device, forming a fibrous construct of entangled cylindrical micelles positioned on a portion of the medical device.

Yet another illustrative embodiment is a method of treating a stenosis of a lumen of a patient. A stent comprising an expandable framework including a plurality of interconnected segments such as undulating segments, wherein a plurality of entangled cylindrical micelles disposed on the expandable framework may be provided. The stent including the plurality of entangled cylindrical micelles may be placed across a stenosis of a lumen, and then the stent may be expanded to engage with the tissue wall of the stenosis. Expansion of the stent may thereby urge the plurality of entangled cylindrical micelles in contact with an inner surface of the lumen. The plurality of cylindrical micelles may be loaded with a therapeutic agent. Thus, once placed at the stenosis, the therapeutic agent may be released (e.g., permeate or diffuse) from the plurality of cylindrical micelles over a duration of time.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in this specification and the appended claims, the term "hydrophilic" refers to the characteristics of readily absorbing or dissolving in water, having polar groups which readily interact with water, and/or having an affinity for water.

As used in this specification and the appended claims, the term "hydrophobic" refers to the characteristics of not readily absorbing or dissolving in water, being adversely affected by water, and/or having little or no affinity for water.

As used in this specification and the appended claims, the term "amphiphilic" refers to the characteristics of having both hydrophilic and hydrophobic properties.

As used in this specification and the appended claims, the term "therapeutically effective amount" refers to that amount of the therapeutic agent sufficient to inhibit cell-proliferation, contraction, migration, hyperactivity, or address other conditions. A therapeutically effective amount may refer to the amount of therapeutic agent sufficient to delay or minimize the onset of symptoms associated with cell proliferation, contraction, migration, hyperactivity, or address other conditions. A therapeutically effective amount may also refer to the amount of the therapeutic agent that provides a therapeutic benefit in the treatment or management of certain conditions such as stenosis or restenosis and/or symptoms associated with stenosis or restenosis.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Figure 1:
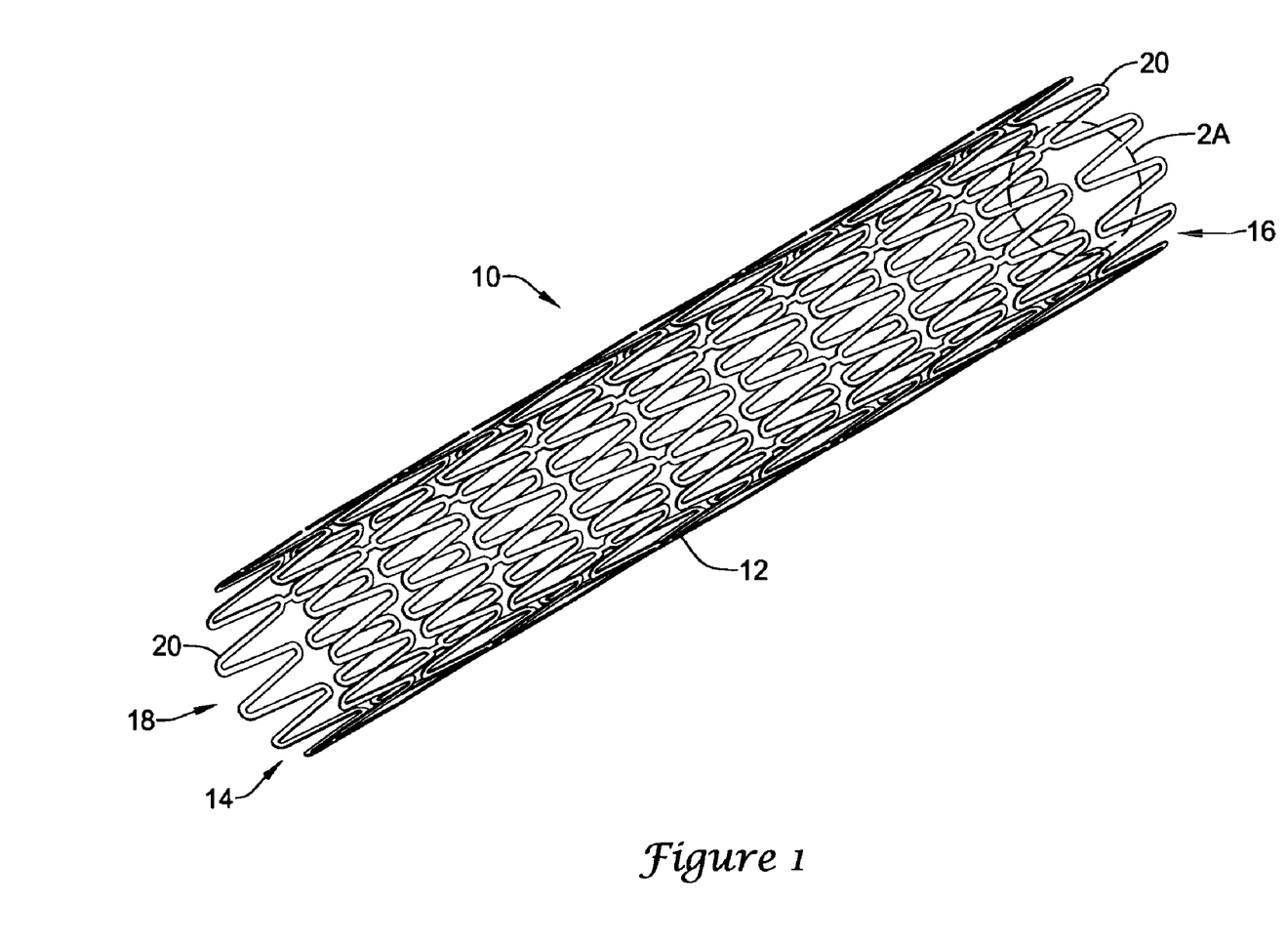
FIG. 1 is an illustrative embodiment of an exemplary stent.

An exemplary implantable medical device, such as a prosthetic graft or endovascular stent incorporating cylindrical micelles included therewith will now be described in more detail. An exemplary implantable medical device, illustrated as an endovascular stent 10, is shown in FIG. 1. Although illustrated as a stent, the implantable medical device may be any of a number of devices that may be introduced subcutaneously, percutaneously or surgically to be positioned within an organ, tissue, or lumen, such as a heart, artery, vein, urethra, esophagus, bile duct, or the like. The stent 10 may be any desired stent, such as an expandable (e.g., self-expandable or mechanically expandable) stent used during a percutaneous transluminal coronary balloon angioplasty (PTCA) or percutaneous transluminal angioplasty (PTA) procedure, for example. Some exemplary stents are disclosed in U.S. Pat. Nos. 6,730,117; 6,776,793; 6,945,993 and 6,981,986, which are each incorporated herein by reference.

The stent 10 may be a generally tubular member having a mesh framework 12 extending between a first end 14 and a second end 16, an outer diameter defining an outer surface, and an inner diameter defining an inner surface forming a lumen 18 extending therethrough. As used herein, the outer surface is intended to refer to the radially outward facing surface of the stent 10 commensurate with the outer diameter of the stent 10. As used herein, the inner surface is intended to refer to the radially inward facing surface of the stent 10 commensurate with the inner diameter of the stent 10. The mesh framework 12 may include a plurality of interconnected segments 20, which can include undulating segments, defining interstitial spaces or openings therebetween. The undulating segments 20 include side surfaces, which may be cut side surfaces formed during process in which material is removed from a workpiece to form the mesh framework 12, extending between the outer surface and the inner surface of the stent 10. The stent 10 may be expandable from a collapsed configuration to an expanded configuration, either independently or by the application of mechanical force. The plurality of segments 20 may be sufficiently flexible in order to be expandable once properly placed at the target site of interest.

The stent 10 may be formed of any desired material, such as a biocompatible material including biostable, bioabsorbable, biodegradable or bioerodible materials. For instance, the stent 10 may be formed of a metallic material or a polymeric material. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof.

The stent 10 may be covered or incorporated with a plurality of cylindrical micelles 50, which may be stabilized as solidified filaments on one or more surfaces (e.g., the outer diameter surface, inner diameter surface or cut side surface) of the expandable framework 12 of the stent 10. (The cylindrical micelles 50 are not illustrated in FIG. 1 for the sake of clarity). Cylindrical micelles are a class of self-assembling structures distinguishable from spherical micelles and vesicles. Cylindrical micelles, otherwise known as worm micelles, are elongate cylindrical bodies, indicative of their name. The cylindrical micelles 50, stabilized as solidified filaments, may be placed on, interwoven with, wrapped around, adhered to, not adhered to, or otherwise incorporated with the stent 10 in any desired fashion.

The plurality of cylindrical micelles 50, which may be stabilized as solidified filaments covering, surrounding or incorporated with the stent 10, are intended to be distinguishable from a coating or laminated layer adhered to and conforming to the outer surface of the stent 10. For example, the plurality of cylindrical micelles 50 may be randomly oriented into a layer or fibrous construct disposed on one or more surfaces of the stent 10. In some embodiments, the layer or fibrous construct of entangled cylindrical micelles 50 may form a bioscaffold structure having a porous structure (e.g., a structure having a plurality of interstitial spaces between filaments), leaving portions of one or more of the surfaces of the expandable framework 12 exposed, visible and/or accessible through the random network of cylindrical micelles 50. Within the layer or fibrous construct, a discrete cylindrical micelle 50 may be readily discernible from an adjacent cylindrical micelle 50, in some embodiments. In other embodiments, the cylindrical micelles 50 may be combined into a unitary mass.

In some embodiments the plurality of cylindrical micelles 50 are nonconforming and/or non-adhered with the outer surface and/or the inner surface of the expandable framework 12. Thus, in some embodiments the plurality of cylindrical micelles 50 may be a three-dimensional fibrous construct or bioscaffold structure having various spaces between adjacent cylindrical micelles 50 surrounding and/or loosely blanketing the expandable framework 12 of the stent 10.

In some embodiments, the plurality of cylindrical micelles 50 may be adhered to or non-adhered to a surface of the expandable framework 12 of the stent 10. Thus, in some embodiments, a layer or fibrous construct of cylindrical micelles 50 may be juxtaposed with and adhered to a surface, such as the outer surface, inner surface, side surface and/or other exposed surface, of the expandable framework 12. In other embodiments, a layer or fibrous construct of cylindrical micelles 50 may be juxtaposed with yet not be adhered to a surface, such as the outer surface, inner surface, side surface and/or other surface, of the expandable framework 12. In some embodiments, the layer or fibrous construct of cylindrical micelles 50 may be retained on the expandable framework 12 through the interaction of the various entangled cylindrical micelles 50 with additional cylindrical micelles 50 enveloping the expandable framework 12.

In some embodiments, the plurality of cylindrical micelles 50 may be disposed conformal with the expandable framework 12. As used herein, conformal is intended to mean that the plurality of cylindrical micelles 50 surround the expandable framework 12 such that cylindrical micelles 50 are disposed on the radially outward facing surface of the stent 10 and disposed on the radially inward facing surface of the stent 10, thus substantially covering the exposed surfaces of the expandable framework 12 of the stent 10. In other embodiments, the plurality of cylindrical micelles 50 may be disposed ablumenal with the expandable framework 12. As used herein, ablumenal is intended to mean that the plurality of cylindrical micelles 50 are disposed on the radially outward facing surface of the stent 10. In yet other embodiments, the plurality of cylindrical micelles 50 may be disposed lumenal with the expandable framework 12. As used herein, lumenal is intended to mean that the plurality of cylindrical micelles 50 are disposed on the radially inward facing surface of the stent 10 defining the lumen 18.

In some embodiments, a surface of the expandable framework 12, such as the outer surface, inner surface, side surface and/or other surface, of the expandable framework 12 may be coated with a primer layer prior to disposing the plurality of cylindrical micelles 50 on the expandable framework 12. In some embodiments the primer layer may be a parylene coating, an acrylate polymer coating, another polymeric coating, or other suitable primer layer. The primer layer may enhance adhesion or otherwise improve interaction of the cylindrical micelles 50 with a surface of the expandable framework 12. Thus, in some embodiments, a primer layer may be interposed between a surface of the expandable framework 12 and a plurality of cylindrical micelles 50, such as a layer or fibrous construct of cylindrical micelles 50. The primer layer may be applied through any suitable process, such as vapor deposition, dip coating, spray coating, or other suitable process.

Figure 2A:
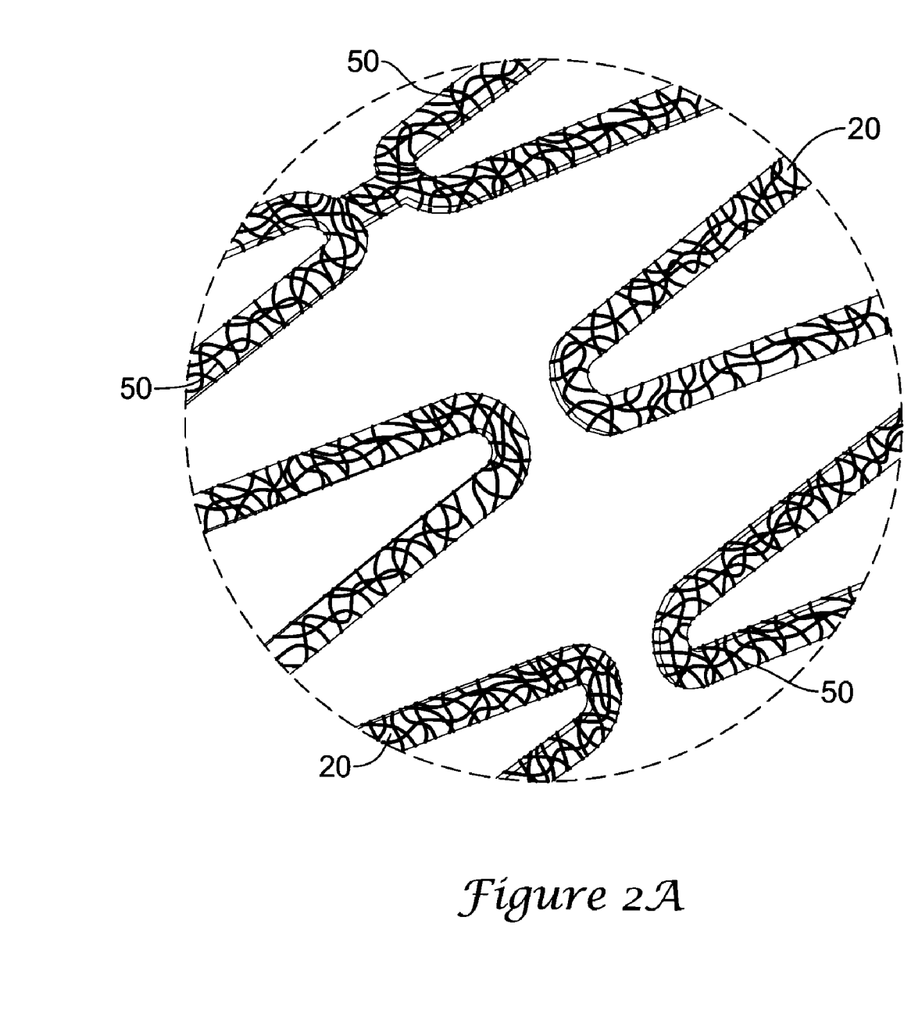
FIG. 2A is an enlarged view of a portion of the stent of FIG. 1 incorporating an arrangement of a plurality of cylindrical micelles.

In some embodiments, such as the embodiment shown in FIG. 2A, which is an expanded view of a portion of the stent 10 incorporating a plurality of cylindrical micelles 50, the cylindrical micelles 50 may be a woven, non-woven and/or entangled layer of filaments disposed on one or more surface portions of the stent 10. As shown in FIG. 2A, in some embodiments the cylindrical micelles 50 may surround or encircle each individual interconnected segment 20 of the expandable framework 12. In some embodiments, the cylindrical micelles 50 may be disposed on the stent 10, leaving a portion of the outer surface and/or inner surface of the framework 12 of the stent 10 exposed and accessible to tissue and/or blood while the stent 10 is in a collapsed state and/or in an expanded state. In some embodiments, the outer surface, inner surface and/or other surface juxtaposed with the layer of micellar filaments of the expandable framework 12 of the stent 10 may be visible and/or accessible through the layer of cylindrical micelles 50 when the stent 10 is retained in a collapsed state, as well as when the stent 10 is in an expanded state. As shown in FIG. 2A, in some embodiments a portion of the outer surface of the expandable framework 12 may be exposed throughout the entanglement of cylindrical micelles 50.

Figure 2B:
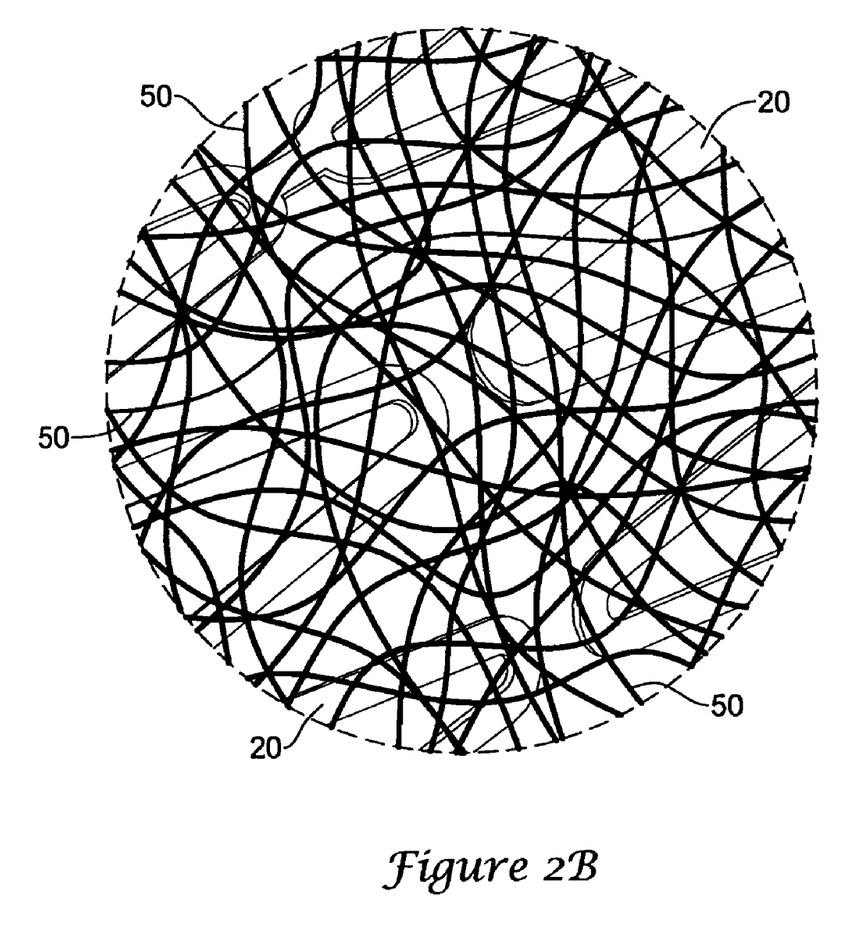
FIG. 2B is an enlarged view of a portion of the stent of FIG. 1 incorporating an alternative arrangement of a plurality of cylindrical micelles.

Another arrangement of cylindrical micelles 50 is shown in FIG. 2B. As shown in FIG. 2B, which is an expanded view of a portion of the stent 10 incorporating a plurality of cylindrical micelles 50, the cylindrical micelles 50 may be a woven, non-woven and/or entangled fibrous construct of filaments placed over the outer surface of the stent 10. As shown in FIG. 2B, in some embodiments the cylindrical micelles 50 may surround or encircle the outer diameter of the expandable framework 12 of the stent 10. Thus, in some embodiments the fibrous construct of cylindrical micelles 50 may extend across the openings formed between adjacent interconnected segments of the expandable framework 12 of the stent 10. In other embodiments, the entangled fibrous construct of filaments may be placed over the inner surface, a side surface, and/or other surface of the stent 10, as desired.

The fibrous construct or bioscaffold of cylindrical micelles 50 may be disposed on the stent 10, leaving a portion of the outer surface and/or inner surface of the framework 12 of the stent 10 exposed and accessible to tissue and/or blood while the stent 10 is in a collapsed state and/or in an expanded state. In some embodiments, the outer surface, or other surface juxtaposed with the fibrous construct of micellar filaments of the expandable framework 12 of the stent 10, may be visible and/or accessible through the fibrous construct of cylindrical micelles 50 when the stent 10 is retained in a collapsed state, as well as when the stent 10 is in an expanded state. As shown in FIG. 2B, in some embodiments, a portion of the outer surface of the expandable framework 12 may be exposed throughout the entanglement of cylindrical micelles 50. In some embodiments, the network of entangled cylindrical micelles 50 may be wrapped around the stent 10, adhered to the stent 10, or not adhered to the stent 10, creating a bioscaffold around the stent 10. In such an instance, spaces between adjacent cylindrical micelles 50 of the dense network may provide visualization and/or accessibility to the outer surface, or other surface, of the expandable framework 12 of the stent 10 juxtaposed with the fibrous construct of micelles 50 when the stent 10 is retained in a collapsed state, as well as when the stent 10 is in an expanded state.

In some embodiments, the diameter of a cylindrical micelle 50 may be between about 1 nanometer to about 1 micrometer, for example. For instance, in some embodiments a cylindrical micelle 50 may have an outer diameter of about 1 nanometer to about 500 nanometers, about 1 nanometer to about 100 nanometers, about 10 nanometers to about 100 nanometers, about 10 nanometers to about 50 nanometers, about 20 nanometers to about 40 nanometers, or about 20 nanometers.

In some embodiments, the length of a cylindrical micelle 50 may be about 0.1 micrometer or more. For instance, in some embodiments, a cylindrical micelle 50 may have a length of about 0.1 micrometer to about 100 micrometers, about 1 micrometer to about 100 micrometers, about 1 micrometer to about 50 micrometers, or about 1 micrometer to about 10 micrometers. However, in some embodiments, a cylindrical micelle 50 may have a length of less than about 0.1 micrometer or a length of greater than about 100 micrometers.

The cylindrical micelles 50 are typically formed of multi-block copolymers, such as amphiphilic copolymers. For instance, the cylindrical micelles 50 may include a first polymer block surrounding a second polymer block. In some instances, the first polymer block may be chosen to be readily soluble in a desired solution, whereas the second polymer block may be chosen to be insoluble or soluble to a lesser degree in the desired solution. In other words the first polymer block may have a differential solubility from the second polymer block in a selective solvent system, wherein the first polymer block has a greater solubility in the selective solvent system than the second polymer block. Since the first polymer block has a greater solubility in the selective solvent system than the second polymer block, the first polymer block tends to assemble around the second polymer block, forming an outer shell region of the first polymer block around a core region of the second polymer block. Thus, the second polymer block found in the core region attempts to dissociate from the selective solvent, whereas the first polymer block found in the outer shell region attempts to associate with the selective solvent.

For instance, in some embodiments the first polymer block may be a hydrophilic polymer block soluble in an aqueous solution, and the second polymer block may be a hydrophobic polymer block insoluble or less soluble in an aqueous solution. In other embodiments, the first polymer block may be a hydrophobic polymeric block, and the second polymer block may be a hydrophilic polymer block. Such a combination may assemble into a cylindrical micelle 50 in a nonpolar solvent, for example. Thus, it can be seen that the relative solubility of the chosen polymer blocks in the select solvent solution directs formation of the cylindrical micelles 50.

The block copolymers may be diblock copolymers, triblock copolymers, or other multi-block copolymers generally known. Thus, the combination of polymer blocks which may be used to form the cylindrical micelles 50 is expansive, taking into account that formation of cylindrical micelles from polymer blocks typically is dependent, at least in part, on the molecular weight fraction of the polymer block forming the outer shell region, such as a hydrophilic block, relative to the molecular weight of the combination of the polymer block forming the outer shell region and the polymer block forming the core region, such as a hydrophobic block.

The cylindrical micelles 50 and/or specific block components of the copolymers of the cylindrical micelles 50 may be biostable, bioabsorbable, or biodegradable. Some suitable block component materials can include, for example, polyesters, polyamides, polyolefins, polyethers, polyurethanes, polyureas, polyvinyl acetates, polyvinyl ketones, polyvinyl ethers, polyacrylics, polyacrylates, polymethacrylates, polycarbonates, polyimides, polyorthoesters, polyanhydrides, polysaccharides, vinyl halide polymers, polyvinylidene halides, polyvinyl aromatics, inorganic polymers, including silicones (e.g., polysiloxanes and substituted polysiloxanes), and fluoropolymers, to name a few.

Specific examples of these block copolymer components include, for example polyisobutylene, polystyrene, polyvinyl alcohol (PVA), polyethylene oxide (PEO), polytetrahydrofuran, phosphatidyl coline based polymers, poly(lactide-co-glycolide) (PLGA), poly(L-lactide) (PLLA), poly(DL-lactide), polyphosphazenes, polycaprolactone (PCL), polyvinyl methyl ether, polyvinylidene fluoride, polyacrylonitrile, polyethylene vinyl acetate, polybutyl methacrylate, polybutyl acrylate, acrylonitrile-styrene copolymers, Nylon 66 and polycaprolactam, cellulose, cellulose acetate, cellulose butyrate, cellulose acetate butyrate, cellophane, cellulose nitrate, cellulose propionate, cellulose ethers, carboxymethyl cellulose, collagens, chitins, polyglycolic acid (PGA), and polylactic acid-polyethylene oxide copolymers, to name a few.

Although in some embodiments the polymers may be chosen for their hydrophilicity or hydrophobicity, in other embodiments the polymers may be chosen for their water solubility, or for their bioabsorbability or biodegradability, for example. Some examples of hydrophilic polymers include poly(ethylene oxide) (PEO), poly(ethylene glycol) (PEG), poly(lactide-co-glycolide) (PLGA), poly(L-lactide) (PLLA), poly(alkylene glycol) (PAG), and poly(vinyl alcohol) (PVA). Some examples of hydrophobic polymers include poly(glycolic acid) (PGA), poly(ethyl ethylene) (PEE), polybutadiene (PBD), polycaprolactone (PCL), and poly(lactic acid) (PLA). Some examples of water soluble polymers include poly(ethylene oxide) (PEO), poly(ethylene glycol) (PEG), and poly (vinyl alcohol) (PVA). Some examples of biodegradable polymers include poly(lactic acid) (PLA), poly(lactide-co-glycolide) (PLGA), poly(lactide-co-caprolactone) (PLC), poly(lactide-co-caprolactone-co-glycolide) (PLCG), and polycaprolactone (PCL).

An assembled cylindrical micelle 50 may have an outer shell or corona of a first polymer block surrounding a core region formed of a second polymer block. The polymer block of the corona or outer shell region is readily soluble in the desired solution, whereas the polymer block of the core region is insoluble or soluble to a lesser degree in the desired solution. For instance, the core region may include a hydrophobic block polymer and the corona or outer shell may include a hydrophilic block polymer, or vise versa. Such an arrangement may be due in that the hydrophobic block attempts to repel the solvent system, while the hydrophilic block is attracted to the surrounding solvent system. Thus, the hydrophobic block tends to assemble in the core region of the cylindrical micelle 50 separated from the solvent system, while the hydrophilic block tends to assemble in the corona or outer shell region of the cylindrical micelle 50 adjoining the solvent system.

Formation of the cylindrical micelles 50 may take place in an aqueous solution, such as water, or other solution in which one of the polymer blocks forming the cylindrical micelle 50 has a higher affinity than the other polymer block. Suspended in an aqueous solution, the hydrophobic polymer block and the hydrophilic polymer block tend to self assemble into micelles. The hydrophobic block tends to assemble in the core region of the cylindrical micelles, with the hydrophilic block forming an outer shell region surrounding the more hydrophobic core region. Formation of cylindrical micelles from polymer blocks may be controlled, at least in part, by the molecular weight fraction of the hydrophilic block relative to the molecular weight of the combination of the hydrophilic block and the hydrophobic block, for example.

Once the cylindrical micelles 50 have stabilized in the solution, the cylindrical micelles 50 may either be directly applied to a stent 10 from the micellar solution, or the cylindrical micelles 50 may be first isolated and subsequently transferred to a stent 10. For instance, in some embodiments the stent 10 may be submerged into the micellar solution such that cylindrical micelles 50 collect on the expandable framework 12 of the stent 10. Alternatively or additionally, cylindrical micelles 50 may be applied to the expandable framework 12 of the stent 10 by spray coating, roll-coating, drop-on-demand processes, electrostatic coating, or the like, for example.

Once the cylindrical micelles 50 have assembled, the cylindrical micelles 50 may undergo a solidification process fixing the cylindrical micelles 50 into filaments. In some embodiments, solidification of the cylindrical micelles 50 may be achieved by rapid evaporation of one or more solvent components resulting in solidification of the micellar core or shell of the cylindrical micelles 50 by glass transition vitrification or polymer recrystallization. Alternatively, micelle solidification may be achieved by chemical cross-linking in some embodiments.

Subsequent to and/or concurrently with formation of the cylindrical micelles 50, the cylindrical micelles 50 may be loaded or filled with a therapeutic agent. For instance, in some embodiments a therapeutic agent may be encapsulated in the core region of the cylindrical micelles 50, a therapeutic agent may be encapsulated in the corona or outer shell region, or a therapeutic agent may be encapsulated in the core region and a therapeutic agent may be encapsulated in the corona or outer shell region. In some embodiments the therapeutic agent may be precipitated from a solution into the cylindrical micelle 50, or the therapeutic agent may be captured and encapsulated within the core region of the cylindrical micelle 50 during assembly of the cylindrical micelle 50 in solution. In other embodiments, the cylindrical micelle 50 may be submerged in or sprayed with a therapeutic agent or a solution including a therapeutic agent.

A wide range of hydrophilic or hydrophobic materials may be loaded with or encapsulated in a cylindrical micelle 50. For example, the cylindrical micelles 50 may be loaded with a therapeutic agent, such as a hydrophilic or a hydrophobic therapeutic agent. Paclitaxel is one suitable hydrophobic therapeutic agent, and heparin or urikinase are suitable hydrophilic therapeutic agents which may be loaded with or encapsulated in a cylindrical micelle 50. For instance, a therapeutic agent may be encapsulated in the core region (e.g., hydrophobic region) and/or the outer shell region (e.g., hydrophilic region) of the cylindrical micelles 50 and/or the interface between the core region and the outer shell region of the cylindrical micelles 50. In some embodiments the cylindrical micelles 50 may include a therapeutically effective amount of one or more therapeutic agents for inhibiting cell proliferation, contraction, migration or hyperactivity, inflammation, thrombosis, restenosis, or the like.

Once implanted in a body, the therapeutic agent may dissipate or diffuse from the cylindrical micelle 50 over a pre-determined period of time dictated, at least in part, by the absorption and/or degradation rate of the cylindrical micelles 50. Thus, in some embodiments the rate of release of the therapeutic agent may be known and dictated, at least in part, by the absorption of the cylindrical micelles 50 and/or the degradation of the cylindrical micelles 50. For instance, the structure of the cylindrical micelles 50 may be chosen to controllably release the therapeutic agent over a period of minutes, hours, days, weeks, months, years, etc. In some embodiments, the duration of release of the therapeutic agent from the cylindrical micelles 50 may be about 1 hour, about 2 hours, about 3 hours, about 4 hours, about 5 hours, about 6 hours, about 12 hours, about 1 day, about 2 days, about 3 days, about 4 days, about 5 days, about 6 days, about 1 week, about 2 weeks, about 3 weeks, about 1 month, about 2 months, about 3 months, about 4 months, about 5 months, about 6 months, about 1 year, about 2 years, or longer. In some embodiments the duration for controlled release of the therapeutic agent may be about 1 hour to about 24 months. Thus, in some embodiments the cylindrical micelles 50 may be chosen for their absorbability and/or degradability such that a desired rate of drug release is provided.

The therapeutic agent may be any medicinal agent which may provide a desired effect. Suitable therapeutic agents include pharmaceuticals, genetic materials, and biological materials. For instance, in some embodiments, the therapeutic agent may include a drug which may be used in the treatment of restenosis. Some suitable therapeutic agents which may be loaded in the cylindrical micelles 50 include, but are not necessarily limited to, antibiotics, antimicrobials, anti-proliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, steroidal and non-steroidal anti-inflammatory agents, angiotensin converting enzyme (ACE) inhibitors, free radical scavengers, and anticancer chemotherapeutic agents.

In some embodiments, the therapeutic agent is useful for inhibiting cell proliferation, contraction, migration, hyperactivity, or addressing other conditions. The term "therapeutic agent" encompasses pharmaceuticals, genetic materials, and biological materials. Non-limiting examples of suitable therapeutic agents include heparin, heparin derivatives, urokinase, dextrophenylalanine proline arginine chloromethylketone (PPack), enoxaprin, angiopeptin, hirudin, acetylsalicylic acid, tacrolimus, everolimus, rapamycin (sirolimus), zotarolimus, picrolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti thrombin antibodies, anti platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, taxol, paclitaxel, 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent is taxol (e.g., Taxol®), or its analogs or derivatives. In another embodiment, the therapeutic agent is paclitaxel. In another embodiment, the therapeutic agent is an immunosuppressant such as everolimus, sirolimus, zotarolimus, tacrolimus, picrolimus, or the like. In yet another embodiment, the therapeutic agent is an antibiotic such as erythromycin, amphotericin, rapamycin, adriamycin, etc. In yet anther embodiment, the therapeutic agent is a drug combination including drug conjugates for targeted delivery and promotion of endocytosis.

The term "genetic materials" means DNA or RNA, including, without limitation, DNA/RNA encoding of a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;

anti-inflammatory agents such as glucocorticoids, betamethasone, dexamethasone, prednisolone, corticosterone, budesonide, estrogen, sulfasalazine, rosiglitazone, mycophenolic acid and mesalamine;

anti-neoplastic/anti-proliferative/anti-miotic agents such as paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, taxol and its analogs or derivatives;

anesthetic agents such as lidocaine, bupivacaine, and ropivacaine;

anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors, antiplatelet agents such as trapidil or liprostin and tick antiplatelet peptides;

DNA demethylating drugs such as 5-azacytidine, which is also categorized as a RNA or DNA metabolite that inhibit cell growth and induce apoptosis in certain cancer cells;

vascular cell growth promoters such as growth factors, vascular endothelial growth factors (VEGF, all types including VEGF-2), growth factor receptors, transcriptional activators, and translational promoters;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin, macrolides such as rapamycin (sirolimus) and everolimuns;

angiogenic substances, such as acidic and basic fibroblast growth factors, estrogen including estradiol (E2), estriol (E3) and 17-beta estradiol; and drugs for heart failure, such as digoxin, beta-blockers, angiotensin-converting enzyme (ACE) inhibitors including captopril and enalopril, statins and related compounds. Preferred biologically active materials include anti-proliferative drugs such as steroids, vitamins, and restenosis-inhibiting agents. Preferred restenosis-inhibiting agents include microtubule stabilizing agents such as Taxol®, paclitaxel (i.e., paclitaxel, paclitaxel analogues, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryltaxol triethanolamine salt, 2'-O-ester with N-(dimethylaminoethyl)glutamine, and 2'-O-ester with N-(dimethylaminoethyl)glutamide hydrochloride salt.

Other preferred therapeutic agents include nitroglycerin, nitrous oxides, nitric oxides, antibiotics, aspirins, digitalis, estrogen derivatives such as estradiol and glycosides.

In certain embodiments, the therapeutic agents for use in the medical devices of the present disclosure can be synthesized by methods well known to one skilled in the art. Alternatively, the therapeutic agents can be purchased from chemical and pharmaceutical companies.

In some embodiments, the cylindrical micelles 50 may be loaded with a mixture of a therapeutic agent and a polymer carrier. Thus elution of the therapeutic agent may be controlled, at least in part, by the degeneration and/or drug releasing properties of the polymer carrier.

The therapeutic agent may be locally released from the cylindrical micelles 50 in a controlled, time-released manner. For instance, the therapeutic agent may be released from the cylindrical micelles 50 over a determined period of time. For instance, the therapeutic agent may permeate from the cylindrical micelles 50 over a period of minutes, hours, days, weeks, months, years, etc. In some embodiments, the rate of absorption and/or degradation of the cylindrical micelles 50 may control the rate of release of the therapeutic agent from the cylindrical micelles 50. For instance a cylindrical micelle 50 having a relatively higher rate of absorption and/or degradation may release the therapeutic agent at a higher rate than a cylindrical micelle 50 having a relatively lower rate of absorption and/or degradation.

The cylindrical micelles 50, with or without the inclusion of a therapeutic agent, may be incorporated with an implantable medical device such as the stent 10 illustrated in FIG. 1 or any other desired medical device in which controlled, drug-releasing capabilities are desired. For instance, the cylindrical micelles 50 may be interwoven with, entwined with, entangled with, wrapped around, adhered to, not adhered to, or otherwise incorporated with the stent 10. The cylindrical micelles 50 may be incorporated with the stent 10 prior to or subsequent positioning the stent 10 on a catheter balloon or other delivery/deployment device.

Figure 3:
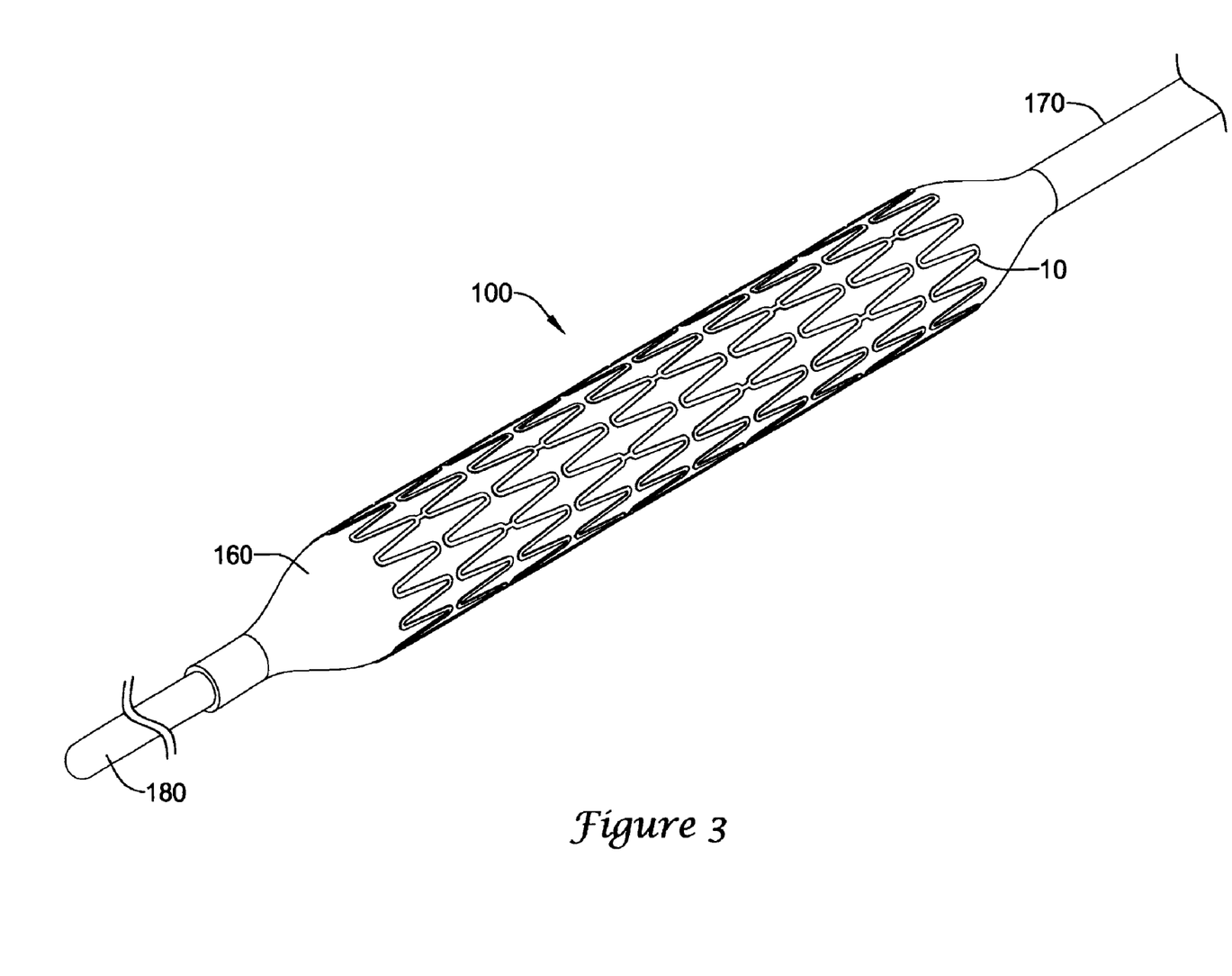
FIG. 3 is an illustrative embodiment of a stent placement system including a stent incorporating a plurality of cylindrical micelles.

FIG. 3 illustrates an exemplary stent placement assembly 100 including a stent 10 incorporating the cylindrical micelles 50 as described herein. (The cylindrical micelles 50 are not illustrated in FIG. 3 for the sake of clarity). The assembly 100 includes an inflatable balloon 160 secured to a catheter shaft 170. The stent 10 may be positioned over the inflatable balloon 160. For example, the stent 10 may be crimped, or otherwise compressed over the inflatable balloon 160. A plurality of cylindrical micelles 50 may be incorporated with the stent 10. For example, in some embodiments the cylindrical micelles 50 may be incorporated with the stent 10 prior to securing the stent 10 over the balloon 160. For instance, in some embodiments the cylindrical micelles 50 may be interwoven and/or entangled with the undulating segments 20 of the stent 10. In other embodiments, the cylindrical micelles 50 may be adhered to and/or encircle the undulating segments 20 of the stent 10. However, in other embodiments the cylindrical micelles 50 may be placed on the stent 10 subsequent to securing the stent 10 over the balloon 160. For instance, in some embodiments the cylindrical micelles 50 may be loosely wound around and/or collected on the stent 10 after the stent 10 is crimped onto the balloon 160, such that the cylindrical micelles 50 are not adhered to the undulating segments 20 of the stent 10. In some embodiments, the cylindrical micelles 50 may form a fibrous construct or bioscaffold over the expandable framework of the stent 10. The fibrous construct may be adhered or not adhered to the expandable framework of the stent 10.

During a medical procedure, a guidewire 180 may be advanced through a lumen, such as a blood vessel, of a patient to a remote location, such as distal a stenosis. The stent placement assembly 100 may be advanced over the guidewire 180 such that the balloon 160 and/or the stent 10 is positioned across the stenosis. The stent 10 may be expanded to engage the tissue surface of the stenosis. For example, the balloon 160 may be expanded in order to expand the stent 10 to contact the tissue of the vessel. Upon expansion of the stent 10, the cylindrical micelles 50 may be interposed between the tissue surface and the stent 10. Subsequently, the catheter 170, including the balloon 160, may be withdrawn from the lumen, leaving the stent 10 in place at the stenosis. Implanted with the stent 10, the cylindrical micelles 50 may promote tissue growth on and/or around the stent 10 and/or provide the controlled-release of a therapeutic agent over a duration of time.

In some embodiments, the cylindrical micelles 50 may be incorporated with a biodegradable polymeric stent structure or a bioerodible metal stent structure, such as a magnesium or iron stent. In such an embodiment, the cylindrical micelles 50 may serve multiple purposes. Initially, the cylindrical micelles 50 may deliver a therapeutic agent to the surrounding tissue as the stent structure is degrading and/or eroding. Additionally or alternatively, the inclusion of the cylindrical micelles 50 may also promote tissue growth around the stent 10 once implanted in a vessel lumen. This may be due, at least in part, to the exposed surface area of the cylindrical micelles 50 as a consequence of the porous nature and large surface area of the fibrous construct or bioscaffold of cylindrical micelles 50. Thus, the porous nature of the fibrous construct of cylindrical micelles 50 may more readily promote tissue growth around the stent 10 than a bare metal stent or instances in which a stent is coated with a polymeric layer of material. Therefore in some instances, it may be desirable to incorporate cylindrical micelles 50 not loaded with a therapeutic agent and/or cylindrical micelles 50 loaded with a therapeutic agent with a stent 10 in order to promote tissue growth around the stent 10.

There are numerous additional perceived advantages of the presently described cylindrical micelles incorporated with a medical device, such as a stent. For instance, adhesion problems commonly encountered with stent coatings are eliminated. Additionally, application of the disclosed cylindrical micelles to the stent does not adversely affect the morphology of the stent material, which may be the case when applying a coating directly to a stent surface.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A stent comprising:
   an expandable framework having a first end, a second end, an outer diameter defining an outer surface, and an inner diameter defining an inner surface forming a lumen, the expandable framework including a plurality of interconnected segments; and
   a plurality of cylindrical micelles incorporated with the expandable framework, the cylindrical micelles formed of multi-block amphiphilic copolymers self-assembling in a solution such that the cylindrical micelles have an outer shell region including a first polymer block of the multi-block amphiphilic copolymer surrounding a core region including a second polymer block of the multi-block amphiphilic copolymer, wherein the first polymer block is more soluble in the solution than the second polymer block.

2. The stent of claim 1, wherein the cylindrical micelles are loaded with a therapeutic agent.

3. The stent of claim 2, wherein the therapeutic agent is encapsulated within the core region of each of the cylindrical micelles.

4. The stent of claim 2, wherein the therapeutic agent is encapsulated within the outer shell region of each of the cylindrical micelles.

5. The stent of claim 2, wherein the therapeutic agent is encapsulated within the outer shell region and the core region of each of the cylindrical micelles.

6. The stent of claim 2, wherein the therapeutic agent includes a drug for the treatment of restenosis.

7. The stent of claim 2, wherein the therapeutic agent includes a drug promoting endocytosis.

8. The stent of claim 1, wherein the plurality of cylindrical micelles are disposed adjacent the inner surface of the expandable framework.

9. The stent of claim 8, wherein a portion of the inner surface of the expandable framework is accessible through the plurality of cylindrical micelles.

10. The stent of claim 1, wherein the plurality of cylindrical micelles are disposed adjacent the outer surface of the expandable framework.

11. The stent of claim 10, wherein a portion of the outer surface of the expandable framework is accessible through the plurality of cylindrical micelles.

12. The stent of claim 1, wherein the plurality of cylindrical micelles surround each interconnected segment of the expandable framework.

13. The stent of claim 1, wherein the plurality of cylindrical micelles are adhered to a surface of the expandable framework.

14. The stent of claim 1, wherein the plurality of cylindrical micelles are not adhered to a surface of the expandable framework.

15. The stent of claim 1, wherein the plurality of cylindrical micelles forms a fibrous structure.

16. The stent of claim 1, wherein the plurality of cylindrical micelles has an average pore size of about 1 nanometer to about 1000 nanometers.

17. The stent of claim 1, wherein each of the cylindrical micelles has a diameter of about 10 nanometers to about 50 nanometers.

18. The stent of claim 1, wherein each of the cylindrical micelles has a length of about 0.1 micrometer to about 100 micrometers.

19. The stent of claim 1, wherein the first polymer block is a hydrophilic block and the second polymer block is a hydrophobic block.

20. The stent of claim 1, wherein the first polymer block is a hydrophobic block and the second polymer block is a hydrophilic block.

* * * * *